US00PP08038P

United States Patent [19]

Matoba

[11] Patent Number: Plant 8,038

[45] Date of Patent: Nov. 24, 1992

[54] "CRIMSON NUGGET" PLUM TREE

[76] Inventor: Frank T. Matoba, 8098 E. American, Del Rey, Calif. 93616

[21] Appl. No.: 722,135

[22] Filed: Jun. 27, 1991

[51] Int. Cl.[5] ..... A01H 5/00

[52] U.S. Cl. ..... Plt./38.1

[58] Field of Search ..... Plt./38.1

[56] References Cited

U.S. PATENT DOCUMENTS

P.P. 2,539 6/1965 Anderson ..... Plt. 38.1
P.P. 3,811 11/1975 Zaiger ..... Plt. 38.1
P.P. 4,823 2/1982 Anderson ..... Plt. 38.1
P.P. 7,765 1/1992 Matoba ..... Plt. 38.1

*Primary Examiner*—James R. Feyrer
*Attorney, Agent, or Firm*—Worrel & Worrel

[57] ABSTRACT

A new and distinct variety of plum tree which is somewhat remotely similar to the "Red Beaut" plum tree with which it is most closely related and from which it was derived, but from which it is distinguished by producing fruit which are mature for harvesting and shipment approximately 5 days prior to the fruit of the "Red Beaut" plum tree.

1 Drawing Sheet

BACKGROUND OF THE NEW VARIETY

The present invention relates to a new and distinct variety of plum tree, which will hereinafter be denominated varietally as the "Crimson Nugget" plum tree and, more particularly, to a plum tree which produces fruit which are mature for commercial harvesting and shipment approximately May 15 to May 20 in the San Joaquin Valley of central California The "Red Beaut" plum tree is well known as the first commercial variety of plum available for harvest ripening approximately May 20 to May 25 in the San Joaquin Valley of central California. As a consequence, the fruit of the "Red Beaut" plum tree frequently serves as the leader in establishing price and shipment levels for subsequently maturing varieties through the harvest season.

Fruit of commercial quality is particularly desirable if its date of maturity is compatible with other commercial varieties ripening during a period in which there is an absence of fruit of comparable character. The commercial desirability of such fruit is enhanced still further if its maturity date is the earliest of all such commercial varieties. This is one of the reasons for the success of the "Red Beaut" plum tree. Therefore, horticulturalists devot significant developmental energy to locating a new variety which ripens even earlier than the earliest known commercial variety. The "Crimson Nugget" plum tree of the present invention is such a new variety maturing approximately five days before the variety of plum tree heretofore known as the earliest ripening commercial variety of plum tree; that is, the "Red Beaut" plum tree.

ORIGIN AND ASEXUAL REPRODUCTION OF THE NEW VARIETY

The present variety of plum tree hereof was discovered by the inventor in 1984 in his orchard, which is located in Del Rey in the San Joaquin Valley of central Calif. The newly found seedling is an opening pollinated seedling of the "Red Beaut" plum tree. The new variety was asexually reproduced in 1986 at the applicant's direction of the same property. The asexually reproduced trees first bore fruit in 1988 and the asexually reproduced trees have been monitored since that time. The asexually reproduced trees have been confirmed to possess precisely the same characteristics as the parent tree.

SUMMARY OF THE VARIETY

The "Crimson Nugget" plum tree is characterized as to novelty by producing a cling fruit of Port Wine coloration and small size which is ripe for commercial harvesting and shipment approximately May 15 to May 20 in the San Joaquin Valley of central California. The new variety is most closely similar to the "Red Beaut" plum tree from which it was derived as an open pollinated seedling, but which is distinguished and characterized principally as to novelty by producing fruit which are ripe for harvesting and shipment approximately five days before "Red Beaut" plum tree.

BRIEF DESCRIPTION OF THE DRAWING

The drawing is a color photograph of fruit of the new variety including a first in bottom plan view showing the apex end thereof, a second sectioned along the suture plane and with the pit removed to expose the pit well, a third sectioned along the suture plane and with the pit left in place, a fourth in side elevation and a fifth in top plan view showing the stem cavity; and foliage and small bunches characteristic of the new variety.

DETAILED DESCRIPTION

Referring more specifically to the pomological details of this new and distinct variety of plum tree, the following has been observed under the ecological conditions prevailing at the orchard of origin which is located in Del Rey in the San Joaquin Valley of central California. All major color code designations are by reference to the Dictionary of Color, by Maerz and Paul, Second Edition, 1950. Common color names are also employed occasionally.

TREE

Generally:

*Size.*—Medium.
*Figure.*—Upright.
*Productivity.*—Productive.
*Regularity of bearing.*—Regular.

Trunk:

*Size.*—Stocky.
*Surface texture.*—Medium, shaggy.

Branches:
*Size.*—Medium.
*Surface texture.*—Rough.
*Color.*—Base color — Page 37, Plate 7, A-7 India Red. Streak color — Page 51, Plate 14, L-10 Antique Bronze.
*Lenticels.*—Numbers — Numerous. Size — 1 mm (0.0393 inches) to 2 mm (0.0787 inches) by 4 mm (0.1575 inches) to 6 mm (0.236 inches).

LEAVES

Size:
*Generally.*—Medium.
*Average length.*—100 mm (3.937 inches) to 118 mm (4.646 inches).
*Average width.*—36 mm (1.417 inches) to 40 mm (1.575 inches).

Form:
*Shape.*—Ovate.

Color:
*Upwardly disposed surface.*—Page 69, Plate 23, J-8, Mt Vernon Green.
*Downwardly disposed surface.*—Page 69, Plate 23, L-6, Cypress Green.

Marginal form:
*Generally.*—Double serrate.

Glandular characteristics: 2 opposite, reniform.

Petiole:
*Length.*—17 mm (0.6693 inches) to 26 mm (1.024 inches).
*Thickness.*—2 mm (0.0787 inches).

Stem glands:
*Number.*—0 to 1.
*Size.*—Small.
*Arrangement.*—Alternate.
*Type.*—Globose.
*Color.*—Brownish.

Stipules: None.

FLOWERS

Flower buds:
*Size.*—Small 4 mm (0.1575 inches).
*Shape.*—Short, conical and plump.
*Surface texture.*—Glabrous.

Flowers:
*Generally.*—Small.
*Date of bloom.*—With "Ambra" and "July Santa Rosa" plum trees.
*Size.*—Generally — 15 mm (0.591 inches) to 20 mm (0.787 inches) when open.
*Petals.*—Color — White.
*Stamens.*—28 to 32.
*Pistil.*—One.

FRUIT

Maturity when described: Ripe for commercial harvesting and shipment approximately May 15 to May 20 and approximately 5 days before the "Red Beaut" plum tree.

Size:
*Generally.*—Small.
*Average diameter.*—47 mm (1.850 inches) to 49 mm (1.929 inches).
*Average diameter transverse in the suture plane.*—45 mm (1.772 inches) to 47 mm (1.850 inches).
*Average diameter transverse and at right angles to the suture plane.*—42 mm (1.654 inches) to 44 mm (1.732 inches).
*Form.*—Uniformity — Uniform. Symmetry — Round, symmetrical.
*Suture.*—Length — 75 mm (2.953 inches). Position — Distinct, slightly depressed.
*Ventral surface.*—Generally — Smooth.
*Stem cavity.*—Generally — Acute. Width — 12 mm (0.472 inches). Depth — 6 mm (0.236 inches). Length — 20 mm (0.787 inches).
*Stem.*—Generally — Length — 10 mm (0.394 inches). Caliper — 2 mm (0.0787 inches).
*Base.*—Shape — Flat.
*Apex.*— Slightly depressed.
*Pistil point.*—Flattened.

Skin:
*Thickness.*—Thin.
*Texture.*—Medium.
*Tendency to crack.*—None.
*Blush color.*—Page 135, Plate 56, L-12, Port wine.
*Pubescence.*—None.

Flesh:
*Flesh color.*—Page 45, Plate 11, I-7, Golden wheat.
*Surface of pit cavity.*—Rough after pit removal.
*Color of pit well.*—Same as flesh.
*Amygdalin.*—None.
*Juice production.*—Juicy.
*Flavor.*—Subacid.
*Aroma.*—Pleasing.
*Texture.*—Tender.
*Fibers.*—Numbers — Moderate.
*Ripening.*—Even.
*Eating quality.*—Good.

Stone:
*Attachment.*—Cling.
*Fibers.*—Numbers — Many.
*Size.*—Diameter — 7 mm (0.276 inches) to 8 mm (0.315 inches). Suture plane — 16 mm (0.630 inches) to 17 mm (0.669 inches). Length — 20 mm (0.787 inches) to 21 mm (0.827 inches).
*Form.*—Generally — Oval, flattened at base.
*Apex.*—Shape — Pointed.
*Color.*—Page 45, Plate 11, I-7, Golden wheat.
*Base.*—Flat.
*Sides.*—Generally — 4 to 5 ridges per side, extending from base to near apex.
*Ridges.*—Jagged.
*Grooves.*—Size — None.
*Dorsal edge.*—Thin.
*Ventral edge.*—Narrow and thin.
*Tendency to split.*—None.

Use: Fresh.
Keeping quality: Good.
Shipping and handling qualities: Good.

Although the new variety of plum tree possesses the described characteristics noted above as a result of the growing conditions prevailing in Del Rey in the San Joaquin Valley of central California, it is to be understood that variations of the usual magnitude and characteristics incident to changes in growing conditions, fertilization, irrigation, pruning and pest control are to be expected.

Having thus described and illustrated my new variety of plum tree, what I claim as new and desire to be secured by Plant Letters Patent is:

1. A new and distinct variety of plum tree substantially as illustrated and described, which is somewhat remotely similar to the "Red Beaut" plum tree from which it was derived as an open pollinated seedling, but from which it is distinguished and characterized principally as to novelty by producing fruit which are mature for commercial harvesting and shipment approximately 5 days before "Red Beaut" plum tree in the San Joaquin Valley of central California.

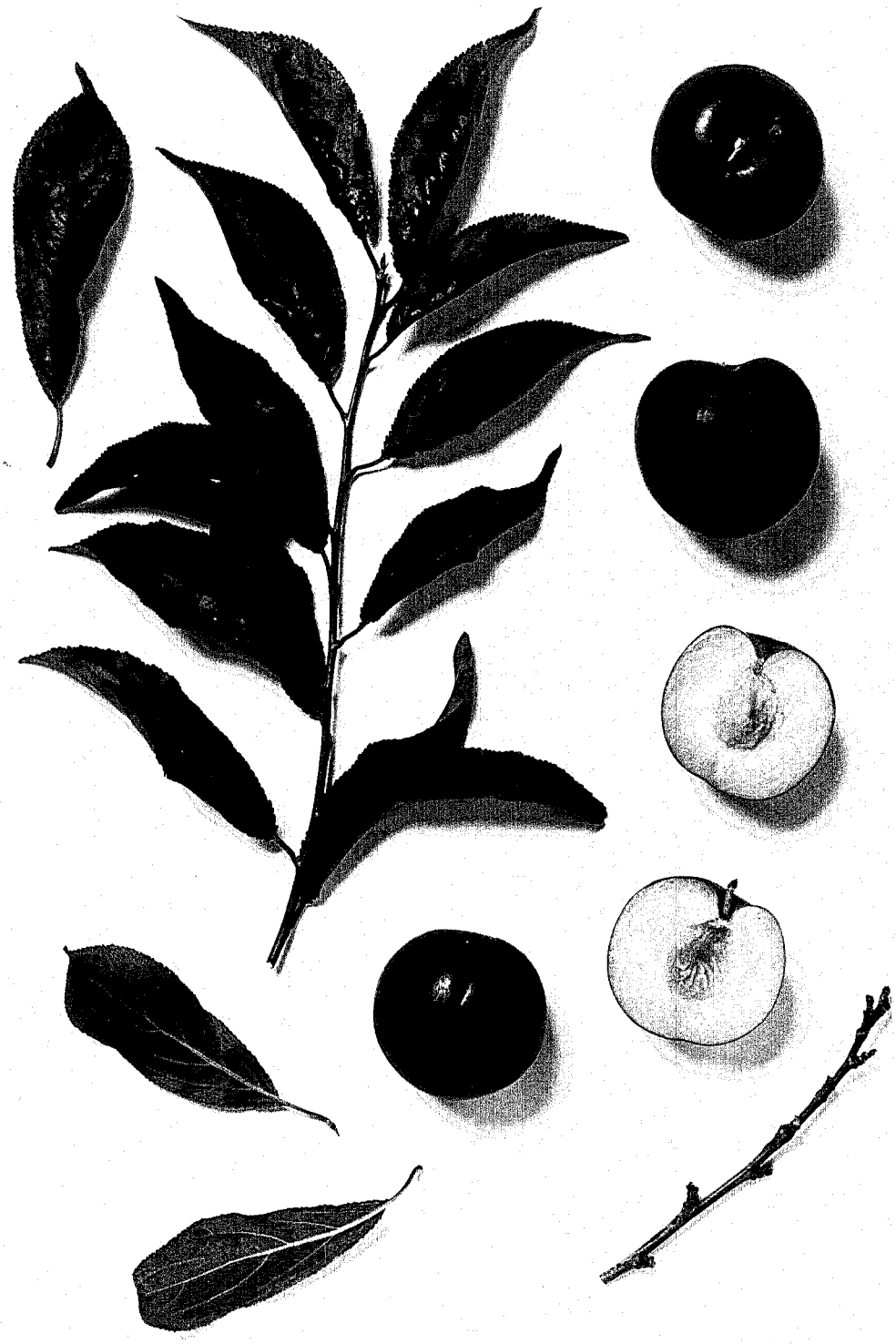

* * * * *